United States Patent
Hua et al.

(10) Patent No.: US 11,480,505 B2
(45) Date of Patent: Oct. 25, 2022

(54) KIT FOR EXTRACTING DRUG RESIDUES FROM LIVESTOCK OR POULTRY AQUATIC PRODUCTS AND METHOD OF OBTAINING PRIMARY TEST LIQUID FROM LIVESTOCK OR POULTRY AQUATIC PRODUCTS USING THE SAME

(71) Applicant: GREAT ENGINEERING TECHNOLOGY CORPORATION, Kaohsiung (TW)

(72) Inventors: Hung-Ta Hua, Kaohsiung (TW); Yi-Jia Ku, Kaohsiung (TW)

(73) Assignee: GREAT ENGINEERING TECHNOLOGY CORPORATION, Kaohsiung (TW)

(*) Notice: Subject to any disclaimer, the term of this patent is extended or adjusted under 35 U.S.C. 154(b) by 333 days.

(21) Appl. No.: 16/657,155

(22) Filed: Oct. 18, 2019

(65) Prior Publication Data
US 2020/0292425 A1 Sep. 17, 2020

(30) Foreign Application Priority Data
Mar. 11, 2019 (TW) .................. 108108078

(51) Int. Cl.
*G01N 1/40* (2006.01)
*G01N 33/12* (2006.01)
(Continued)

(52) U.S. Cl.
CPC ......... *G01N 1/4055* (2013.01); *G01N 1/4077* (2013.01); *G01N 33/04* (2013.01);
(Continued)

(58) Field of Classification Search
CPC ........ G01N 33/04; G01N 33/08; G01N 33/12; G01N 2001/4088; G01N 2001/4061; G01N 2001/4055; G01N 2001/4077
See application file for complete search history.

(56) References Cited

U.S. PATENT DOCUMENTS

| 6,541,273 B1 * | 4/2003 | Plaisance | B01D 15/265 210/198.2 |
| 7,666,686 B2 * | 2/2010 | Shelly, Jr. | G01N 1/405 436/178 |

(Continued)

FOREIGN PATENT DOCUMENTS

| CN | 103884790 A | * | 6/2014 |
| CN | 105319292 A | * | 2/2016 |

(Continued)

OTHER PUBLICATIONS

Hsiang-Yu Liu, et al., Determination of chloramphenicol, thiamphenicol and florfenicol in milk and honey using modified QuEChERS extraction coupled with polymeric monolith-based capillary liquid chromatography tandem mass spectrometry, Department of Chemistry, Soochaw University, Talanta 150 (2016) 233-239.

*Primary Examiner* — Natalie Huls
(74) *Attorney, Agent, or Firm* — WPAT, PC

(57) ABSTRACT

A kit for extracting drug residues from livestock or poultry aquatic products according to the present disclosure includes a pipe, a first powder mixture layer and a second powder mixture layer. The pipe has an output port at the bottom thereof and an input port at the top thereof for inputting a sample solution. The first powder mixture layer is in the form of powder and filled in the pipe. The first powder mixture layer contains anhydrous sodium sulfate powder and sodium chloride powder. The second powder mixture layer is in the form of powder and filled in the pipe. The second powder mixture layer is located below the first (Continued)

powder mixture layer and above the output port. The second powder mixture layer contains anhydrous sodium sulfate powder and C18 powder. The present disclosure further provides a method of obtaining a primary test liquid from livestock or poultry aquatic products using the above kit.

12 Claims, 2 Drawing Sheets

(51) Int. Cl.
 *G01N 33/08* (2006.01)
 *G01N 33/04* (2006.01)
(52) U.S. Cl.
 CPC ............ *G01N 33/08* (2013.01); *G01N 33/12* (2013.01); *G01N 2001/4061* (2013.01); *G01N 2001/4088* (2013.01)

(56) References Cited

U.S. PATENT DOCUMENTS

| | | | | |
|---|---|---|---|---|
| 9,581,579 | B2* | 2/2017 | Lin | ............... G01N 1/405 |
| 11,156,534 | B2* | 10/2021 | Lee | ............... G01N 1/34 |
| 2009/0042240 | A1* | 2/2009 | Stark | ............... C12Q 1/18 |
| | | | | 435/32 |

FOREIGN PATENT DOCUMENTS

| | | | | | |
|---|---|---|---|---|---|
| CN | 105866311 | A | * | 8/2016 | |
| CN | 107389835 | A | * | 11/2017 | ............. G01N 30/06 |
| CN | 108152420 | A | * | 6/2018 | |
| CN | 109580827 | A | * | 4/2019 | |
| CN | 111060638 | A | * | 4/2020 | ............. G01N 33/15 |
| CN | 212410215 | U | * | 1/2021 | |
| CN | 113702558 | A | * | 11/2021 | |

\* cited by examiner

KIT FOR EXTRACTING DRUG RESIDUES FROM LIVESTOCK OR POULTRY AQUATIC PRODUCTS AND METHOD OF OBTAINING PRIMARY TEST LIQUID FROM LIVESTOCK OR POULTRY AQUATIC PRODUCTS USING THE SAME

RELATED APPLICATION

The present application is based on and claims priority to Taiwanese Application Number 108108078, filed Mar. 11, 2019, the disclosure of which is hereby incorporated by reference herein in its entirety.

BACKGROUND

1. Technical Field

This disclosure relates to a quick extraction kit and method of obtaining primary test liquid using the same, and more particularly relates to a kit for extracting drug residues from livestock or poultry aquatic products and method of obtaining primary test liquid from livestock or poultry aquatic products using the same.

2. Description of the Related Art

A veterinary drug is a substance that deals with the prevention, diagnosis and treatment of disease, disorder and injury in animals. In general, food animals include meat-producing or milk-producing animals, poultry, fish and bees.

Animals also get sick like humans and therefore need appropriate treatment. Veterinary drugs can be used to control disease in animals so as to produce food efficiently. In the absence of proper treatment, diseases in animals can affect or reduce production and ultimately reduce the quantity and quality of food. In addition to use as a treatment animal husbandry may also use veterinary drugs to improve feed performance, increase production and promote growth.

Veterinary drugs break down into other substances over time when being applied to animals. However, veterinary drugs will also leave as residues in the animals. Residues of veterinary drugs refer to veterinary drug residues left on animals in a certain period of time after application. These residues may be veterinary drugs themselves or decomposed substances. Residues of veterinary drugs in food may have adverse effects on human health.

In order to detect the amount of veterinary drug residues in food, many extraction kits have been developed. However, current detection of different types of veterinary drug residues uses different extraction kits and detection method.

For example, in order to detect the residual amount of animal drugs such as sulfa drugs, receptors and tetracycline in food, the government has announced different extraction kits and detection methods.

SUMMARY

In order to solve the problem of using different extraction kits and methods of detecting different kinds of veterinary drug residues in food, the present disclosure provides a kit for extracting drug residues from livestock or poultry aquatic products and a method of obtaining primary test liquid from livestock or poultry aquatic products using the same.

In one embodiment, the kit for extracting drug residues from livestock or poultry aquatic products according to the present disclosure includes a pipe, a first powder mixture layer and a second powder mixture layer. The pipe has an output port at the bottom thereof and an input port at the top thereof for inputting a sample solution. The first powder mixture layer is in the form of powder and filled in the pipe. The first powder mixture layer contains anhydrous sodium sulfate powder and sodium chloride powder. The second powder mixture layer is in the form of powder and filled in the pipe. The second powder mixture layer is located below the first powder mixture layer and above the output port. The second powder mixture layer contains anhydrous sodium sulfate powder and C18 powder.

In another embodiment, the method of obtaining a primary test liquid from a livestock or poultry aquatic sample includes the steps: homogenizing the sample; shaking the homogenized sample with an extraction solvent to obtain a sample solution; adding the sample solution into the pipe of the above kit; and driving the sample solution in the pipe to flow through the first powder mixture layer and the second powder mixture layer in the pipe in sequence to output from the output port of the pipe a primary test liquid.

When the kit of the present disclosure is used to obtain primary test liquid from 20 samples, the consumption of the extraction solvent may be saved by 35-90%, and the operation time for extraction may be saved by 80-95%.

Furthermore, according to the kit of the present disclosure and the method of obtaining the primary test liquid, 7 to 10 types of animal drug residues in food, including sulfonamides, quinolones, ionic anticoccidial drugs, antiprotozoal agents, tetracyclines, receptors, and cephalosporins may be simultaneously detected. In comparison with the current government announcement method, detection of different types of drug residues needs different detection methods.

The foregoing, as well as additional objects, features and advantages of the disclosure will be more readily apparent from the following detailed description, which proceeds with reference to the accompanying drawings.

DETAILED DESCRIPTION OF THE PREFERRED EMBODIMENT

Figure 1:
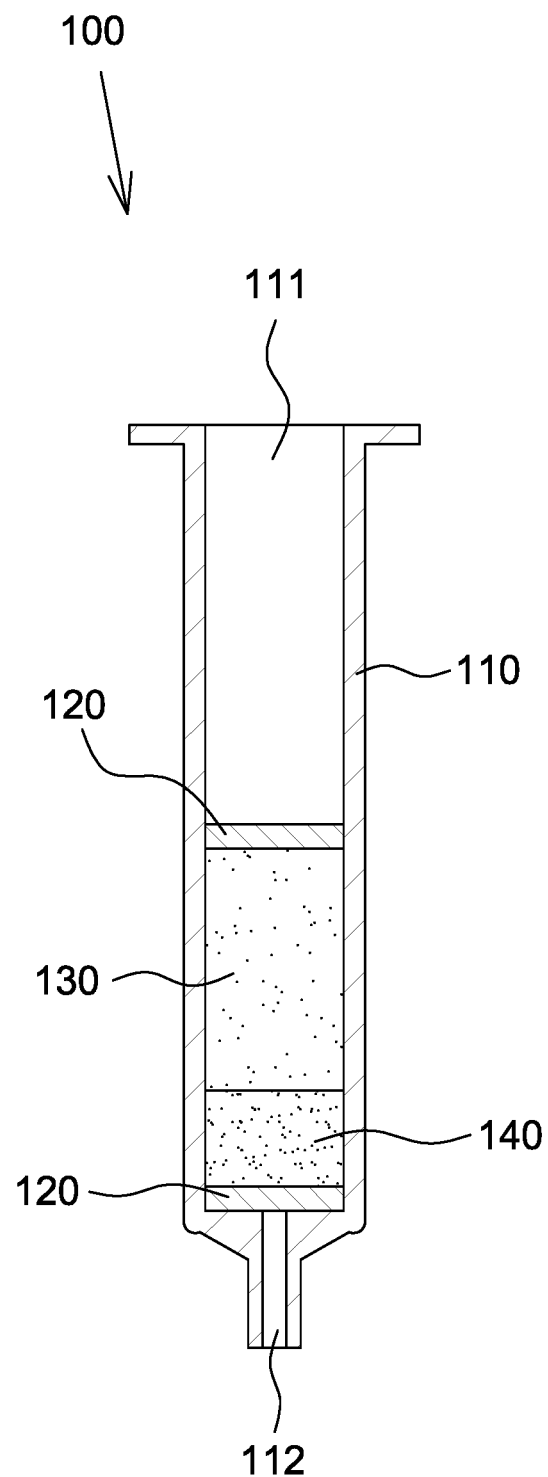
FIG. 1 is a schematic diagram of an extraction kit according to a preferred embodiment of the present disclosure.

Referring to FIG. 1, there is shown an extraction kit 100 of the present disclosure for extracting drug residues from livestock or poultry aquatic products. The extraction kit 100 for extracting drug residues from livestock or poultry aquatic products of the present disclosure includes a pipe 110, a first powder mixture layer 130 filled in the pipe 110 and a second powder mixture layer 140 filled in the pipe 110. The pipe 110 is preferably a cylindrical pipe having an output port 112 at the bottom thereof and an input port 111 at the top thereof. The first powder mixture layer 130 is located below the input port 111, and the second powder mixture layer 140 is located below the first powder mixture layer 130 and above the output port 112. Besides, the extraction kit 100 of the present disclosure further includes two filter pads 120, wherein one of the filter pads 120 is fixed on the top surface of the first powder mixture layer 130 and the other filter pad 120 is fixed on the bottom surface of the second powder mixture layer 140. The top surface of the second powder mixture layer 140 is in direct contact with the first powder mixture layer 130. Alternatively, a filter pad (not shown in the figure) may be further inserted between the first powder mixture layer 130 and the second powder mixture layer 140 to prevent them from mixing.

The extraction kit 100 mentioned above is used in a procedure of detecting drug residues in livestock or poultry aquatic products. This procedure includes the method of obtaining a primary test liquid from a livestock or poultry aquatic sample using the extraction kit 100 of the present disclosure. The method includes the following steps.

The livestock or poultry aquatic sample is first homogenized by using a homogenizer so that the sample is processed into fragments of the livestock or poultry aquatic sample. The livestock or poultry aquatic samples are taken from cattle, pigs, chickens, fish, shrimps, eggs, cattle and goat milk and other livestock or poultry aquatic samples, such as viscera, for use as detecting samples of drug residue detection.

Figure 2:
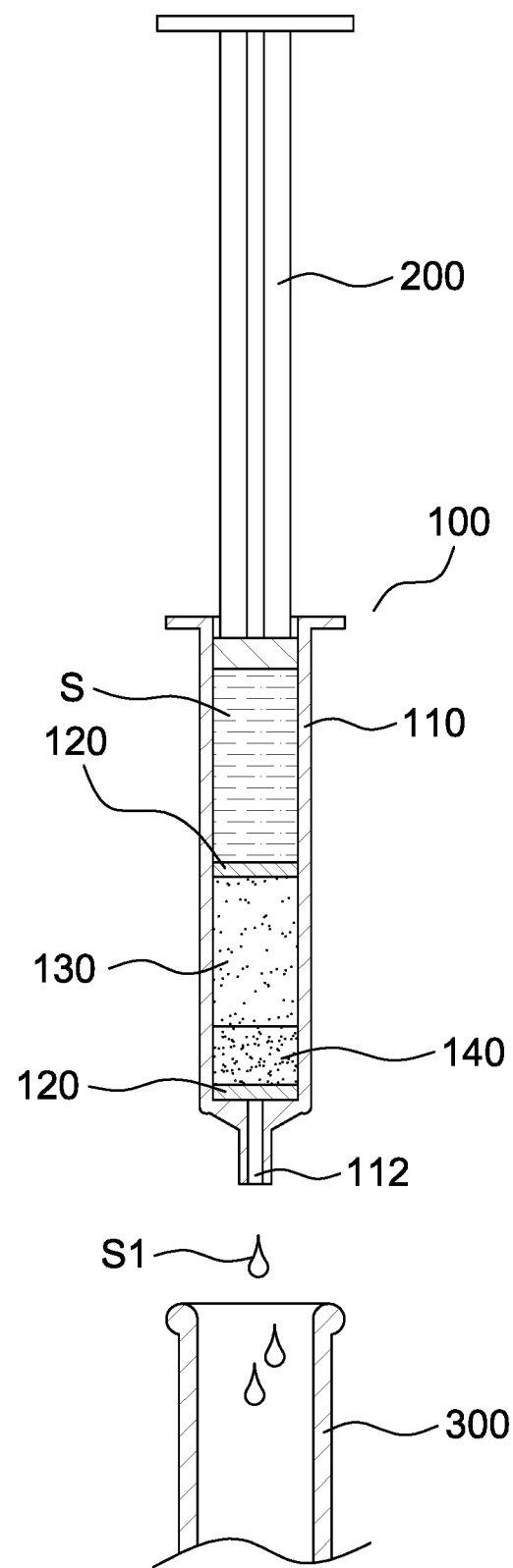
FIG. 2 is another schematic diagram of an extraction kit according to a preferred embodiment of the present disclosure.

Afterward, an extraction solvent is added to the above livestock or poultry aquatic sample and shaken strongly to obtain a sample solution S. A 2~(5±0.03) grams of the livestock or poultry aquatic sample needs to be added 1 to 10 mL of extraction solvent. The extraction solvent is selected from acid-containing acetonitrile methanol, 0.05 mol/L hydrochloric acid, 0.1 mol/L EDTA-2Na or acid-containing acetonitrile solution. A 2~(5±0.03) grams of the livestock or poultry aquatic sample is preferably added with 5 mL of the aforementioned extraction solvent. The extraction solvent is preferably an acetonitrile solution containing 1% acetic acid. The sample solution S is then added into the pipe 110 of the extraction kit 100, as shown in FIG. 2.

Finally, the sample solution S in the pipe 110 is driven to flow through the first powder mixture layer 130 and the second powder mixture layer 140 in sequence so as to output a primary test liquid from the output port 112 of the pipe 110. One of the ways of driving the sample solution S to flow through the first powder mixture layer 130 and the second powder mixture layer 140 in sequence is to press a piston rod 200 to drive the sample solution S to flow. In addition, an air exhausting method may also be used to drive the sample solution S in the pipe 110 to flow through the first powder mixture layer 130 and the second powder mixture layer 140 in sequence. In the air exhausting method a suction device including a vacuum pump (not shown in the figures) is used to connect the output port 112. The vacuum pump is then powered to suck the sample solution S in the pipe 110 to flow out of the output port 112. A flow rate of the sample solution S is preferably controlled to a range of 0.01 to 0.2 mL/sec, more preferably to 0.05 mL/sec. It is to be noted that the filter pads 120 mentioned above should be one without affecting the aforementioned flow rate.

The powder mixture in the first powder mixture layer 130 is able to adsorb most of the water in the sample solution S. Therefore, most of the water in the sample solution S is kept in the first powder mixture layer 130 after the sample solution S flows through the first powder mixture layer 130. Furthermore, the powder mixture in the second powder mixture layer 140 is able to adsorb the remaining water in the sample solution S and the impurities, such as oil or pigment, which may interfere with the instruments when the sample solution S flows through the second powder mixture layer 140. Therefore, after the sample solution S flows through the second powder mixture layer 140, it will form a primary test liquid S1 without impurities or with few impurities. The primary test liquid S1 may be collected with a tube 300.

The primary test liquid S1 may be directly detected by a liquid chromatograph tandem mass spectrometer (LC/MS/MS) to ensure that the drug residues in the sample comply with a requirement. Alternatively, the primary test liquid S1 may also be subjected to a step of air-drying, a step of adding acetonitrile water and a step of filtering with a filter in sequence and then be detected by a liquid chromatography tandem mass spectrometer (LC/MS/MS).

The total weight of the first powder mixture layer 130 is 0.4 to 8 grams, preferably 4.5 grams. The pipe 110 has a selected inner diameter so that the first powder mixture layer 130 has not been pressed tightly and is loose or fluffy during a process of being filled in the pipe 110 with the selected inner diameter. From the viewpoint of volume, the first powder mixture layer 130 has an area of 0.6 to 7.1 $cm^2$ in the pipe 110, preferably 1.13 $cm^2$, and a height of 1 to 8 cm, preferably 4.61 cm. Therefore, the total volume of the first powder mixture layer 130 is preferably 5.8 $cm^3$ and the density of the first powder mixture layer 130 is preferably 0.86 $g/cm^3$. Further, the first powder mixture layer 130 has a porosity of 35 to 70% in the pipe 110, preferably 50% to 62%, so that the flow rate of the sample solution S flowing through the first powder mixture layer 130 may be controlled in an expected range. This makes most of the water in the sample solution S removed by the first powder mixture layer 130.

The above porosity is defined as (the total volume of the first powder mixture layer 130 filled in the pipe 110−the real volume of the first powder mixture layer 130)/(the total volume of the first powder mixture layer 130 filled in the pipe 110)×100%.

In the present disclosure, the powder component used in the first powder mixture layer 130 includes anhydrous sodium sulfate ($Na_2SO_4$) and sodium chloride (NaCl). The anhydrous sodium sulfate and sodium chloride are uniformly mixed in the first powder mixture layer 130. Further, the first powder mixture layer 130 is preferably a mixture of anhydrous sodium sulfate powder and sodium chloride powder, and the weight ratio of the anhydrous sodium sulfate to the sodium chloride in the first powder mixture layer 130 is (3~5):1, preferably 3.5:1.

In the present disclosure, the second powder mixture layer 140 has a weight of 0.2 to 3.6 grams, preferably 2.1 grams. From the viewpoint of volume, the second powder mixture layer 140 has an area of 0.6 to 7.1 $cm^2$ in the pipe 110, preferably 1.13 $cm^2$, and a height of 0.23 to 5 cm, preferably 2.0 cm.

In the present disclosure, the powder component used in the second powder mixture layer 140 includes Octadecylsilane (C18) powder and anhydrous sodium sulfate powder. The C18 and anhydrous sodium sulfate are uniformly mixed in the second powder mixture layer 140. Further, the second powder mixture layer 140 is preferably a mixture of C18 powder and anhydrous sodium sulfate powder, and the weight ratio of the anhydrous sodium sulfate to the C18 in the second powder mixture layer 140 is (1.5~3):1, preferably 2:1.

It is apparent from the above description that the sample solution S composed of the sample fragments and the extraction solvent may be directly extracted by using the extraction kit 100 of the present disclosure to obtain a primary test liquid. With the use of the extraction kit 100 of the present disclosure, the time taken to obtain a primary test liquid from a livestock or poultry aquatic product may be greatly reduced. Therefore, the detection of drug residues in the sample may be performed quickly.

For example, when the extraction kit of the present disclosure is used to obtain primary test liquid from 20 samples, the consumption of the extraction solvent may be saved by 35-90%, and the operation time for extraction may be saved by 80-95%.

Furthermore, according to the extraction kit of the present disclosure and the method of obtaining the primary test liquid, 7 to 10 types of animal drug residues in food, including sulfonamides, quinolones, ionic anticoccidial drugs, antiprotozoal agents, tetracyclines, receptors, and cephalosporins may be simultaneously detected. In comparison with the current government announcement method, detection of different types of drug residues needs different detection methods.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A method of obtaining a primary test liquid from a livestock or poultry aquatic sample, comprising:
   providing a kit, the kit comprising:
      a pipe having an output port at a bottom thereof and an input port at a top thereof;
      a first powder mixture layer filled in the pipe, the first powder mixture layer including a mixture of anhydrous sodium sulfate powder and sodium chloride powder; and
      a second powder mixture layer filled in the pipe and positioned between the first powder mixture layer and the output port, the second powder mixture layer including a mixture of C18 powder and anhydrous sodium sulfate powder;
   homogenizing the sample;
   shaking the homogenized sample with an extraction solvent to obtain a sample solution, wherein the extraction solvent is EDTA-2Na;
   adding the sample solution into the pipe of the kit from the input port; and
   driving the sample solution in the pipe to flow through the first powder mixture layer and the second powder mixture layer in the pipe in sequence to output from the output port of the pipe a primary test liquid.

2. The method as claimed in claim 1, wherein a (2~5) ±0.03 grams of the sample is added to 1 to 10 mL of the extraction solvent.

3. The method as claimed in claim 1, wherein a (2~5) ±0.03 grams of the sample is added to 5 mL of the extraction solvent.

4. The method as claimed in claim 1, wherein a flow rate of the sample solution is controlled in a range of about 0.01 to 0.2 mL/sec.

5. The method as claimed in claim 4, wherein the flow rate of the sample solution is controlled to 0.05 mL/sec.

6. The method as claimed in claim 1, wherein a weight ratio of the anhydrous sodium sulfate to the sodium chloride in the first powder mixture layer is (3~5):1.

7. The method as claimed in claim 1, wherein a weight ratio of the anhydrous sodium sulfate to the C18 in the second powder mixture layer is (1.5~3):1.

8. The method as claimed in claim 6, wherein the weight ratio of the anhydrous sodium sulfate to the sodium chloride in the first powder mixture layer is 3.5:1.

9. The method as claimed in claim 7, wherein the weight ratio of the anhydrous sodium sulfate to the C18 in the second powder mixture layer is 2:1.

10. The method as claimed in claim 1, wherein the first powder mixture layer has a porosity of 35 to 70% in the pipe.

11. The method as claimed in claim 1, wherein the first powder mixture layer has an area of 0.6 to 7.1 cm$^2$ and a height of 1 to 8 cm in the pipe.

12. The method as claimed in claim 1, wherein the second powder mixture layer has an area of 0.6 to 7.1 cm$^2$ and a height of 0.23 to 5 cm in the pipe.

* * * * *